(12) United States Patent
Schneider

(10) Patent No.: US 6,169,204 B1
(45) Date of Patent: Jan. 2, 2001

(54) PHOSPHORIC ACID SALTS OF AN AROMATIC DIAMINE

(75) Inventor: Heinrich Schneider, deceased, late of Ingelheim (DE), by Margarete Schneider, legal representative

(73) Assignee: Boehringer Ingelheim Pharma KG, Ingelheim (DE)

( * ) Notice: Under 35 U.S.C. 154(b), the term of this patent shall be extended for 0 days.

(21) Appl. No.: 09/533,482

(22) Filed: Mar. 23, 2000

(30) Foreign Application Priority Data

Apr. 17, 1999 (DE) .............................................. 199 17 526

(51) Int. Cl.$^7$ .................................................. C07C 211/00
(52) U.S. Cl. ............................................. 564/305; 564/438
(58) Field of Search ...................................... 564/305, 438

(56) References Cited

U.S. PATENT DOCUMENTS 3,819,642 * 6/1974 Strehlke .
3,996,213 * 12/1976 Schinzel .
5,149,700 * 9/1992 Ellingboe et al. .

* cited by examiner

*Primary Examiner*—Samuel Barts
(74) *Attorney, Agent, or Firm*—R. P. Raymond; M-E. M. Devlin; A. R. Stempel

(57) ABSTRACT

The present invention relates to a phosphoric acid salt of N-methyl-o-phenylenediamine and processes for making the same. In preferred embodiments of the invention, the phosphoric acid salt of N-methyl-o-phenylenediamine has the general Formula I

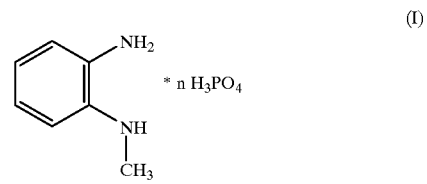

wherein n is a number between 0.5 and 1.0, between 0.7 and 0.8, or between 0.75 and 0.78. The process for making the phosphoric acid salt of N-methyl-o-phenylenediamine comprises (a) dissolving the N-methyl-o-phenylenediamine in a first solvent, and (b) reacting the dissolved N-methyl-o-phenylenediamine with crystalline phosphoric acid or phosphoric acid dissolved in a second solvent.

22 Claims, No Drawings

PHOSPHORIC ACID SALTS OF AN AROMATIC DIAMINE

FIELD OF THE INVENTION

The present invention relates to new phosphoric acid salts of N-methyl-o-phenylenediamine and processes of preparing the same.

BACKGROUND OF THE INVENTION

Aromatic amines are important intermediate compounds for the synthesis of dyes, antioxidants, and particularly pharmaceuticals. Aromatic 1,2-diamines, in particular, are of great industrial importance for the manufacture of aromatic heterocycles, especially those with two heteronitrogen atoms, such as benzimidazoles. These and the salts thereof are of great interest owing to their pharmacological versatility, although it is known that aromatic amines such as aniline are highly prone to oxidation. This makes it particularly difficult to store these compounds. This property is particularly noticeable with liquid aromatic amines of those dissolved in a liquid. Even in the presence of small traces of oxygen or light, these solutions turn deep black after only a short time. This high oxidation sensitivity of the aromatic amines means that they can only be used in further chemical reactions when freshly purified, usually freshly distilled. The oxidation sensitivity of these substances can be reduced by converting the aromatic amines into their salts. Even the salts, however, are usually still sufficiently prone to oxidation that they have to be stored in the absence of oxygen, for example. Such salts also have a tendency to hygroscopy. The most common salts are the hydrohalides, particularly the hydrochlorides.

The phenylenediamines are particularly oxidation-prone. Thus, in the *Reports of the German Chemical Society*, Volume 25, pages 2841–2842, O. Fischer states that the oily N-methyl-o-phenylenediamine "turns dark incredibly quickly and after just a short time becomes totally black even in dark, well-sealed bottles." According to O. Fischer, even the dihydrochloride is a substance which is "relatively sensitive to air and light" (O. Fischer, loc. cit.). The same is true of other salts of N-methyl-o-phenylenediamine known from the prior art, salts of o-phenylenediamine itself, and other salts of mono-, di- and tri-N-alkylated phenylenediamines.

In addition to their high sensitivity to oxidation and light, and in some cases the marked hygroscopy of the hydrohalides of the above-mentioned phenylenediamines, these compounds have other serious disadvantages for use in large-scale industrial processes. Since the salts generally have to be converted into the free base in situ when they are reacted further, the corresponding halohydric acid is formed as a by-product. This is particularly detrimental when the reaction mixture is at a temperature at which hydrohalic acid is produced in gas form. Since these gases are corrosive, highly caustic, and consequently toxic, they have to be carefully removed from the reaction. In some cases this can only be done with considerable technical input, which is accompanied by high costs.

However, not only the use but also the preparation of the salts of phenylenediamines with hydrohalic acids involves some problems on the industrial scale. It would be most convenient if the hydrogen halide were supplied in gas form to the corresponding phenylenediamine in order to minimize losses of yield. This is extremely laborious from a technical point of view, however, with the result that the salts have to be formed from the aqueous hydrohalic acids and high losses of yield have to be accepted.

DESCRIPTION OF THE INVENTION

It is an aim of the present invention to minimize the problems known from the prior art connected with the preparation, storage, and use of N-methyl-o-phenylenediamine.

A further object of the invention is to convert N-methyl-o-phenylenediamine into a form which is easy to handle, with low sensitivity to oxidation and/or light and/or which is not hygroscopic and is easy to store, such that the free bases are rapidly available for subsequent reactions.

DETAILED DESCRIPTION OF THE INVENTION

Surprisingly, it has been found that the salt of N-methyl-o-phenylenediamine and phosphoric acid does not have the disadvantages and consequent problems known from the prior art for other salts of this kind or has them only to a significantly reduced extent.

Thus, the present invention solves the problem by converting N-methyl-o-phenylenediamine into a phosphoric acid salt according to Formula I

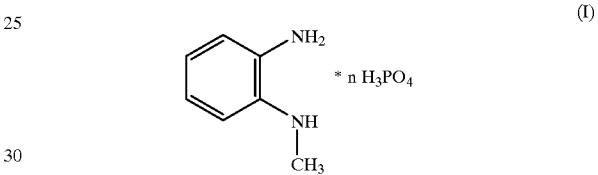

(I)

wherein n is a number between 0.5 and 1.0.

The term "phosphoric acid salt" denotes all salts of N-methyl-o-phenylenediamine with ortho-phosphoric acid ($H_3PO_4$). The ratio of one molecule of $H_3PO_4$ to one molecule of N-methyl-o-phenylenediamine according to Formula I is described as a statistical mean by the factor n.

A salt as described above wherein n is from 0.7 to 0.8 is preferred; most preferably, n equals 0.75 to 0.78.

In a particularly preferred embodiment, the phosphoric acid salts of N-methyl-o-phenylenediamine according to the invention are anhydrous or contain only slight traces of water. The water content of the salt is generally between 1.0 and 1.5% by weight.

The advantages of the phosphoric acid salts of N-methyl-o-phenylenediamine according to the invention consist on the one hand in its resistance to oxidation, insensitivity to light, and non-hygroscopic characteristics. As a result, it is easily stored without any major expense and can be used in further reactions without additional measures, with the optional exception of conversion into the free base. Moreover, it is surprisingly easy to manufacture on a large scale since the phosphoric acid used can be added in the form of crystals. Furthermore, when the phosphoric acid salt itself is further used at elevated temperatures, no caustic or corrosive gases are produced under the reaction conditions.

According to another aspect of the invention, the present invention relates to the industrial-scale manufacture of the N-methyl-o-phenylenediamine-phosphoric acid salt described above.

The salt is easily obtainable in high yields by dissolving N-methyl-o-phenylenediamine in a water- or alcohol-miscible solvent such as a $C_1$- to $C_5$-alcohol, preferably ethanol, propanol, or isopropanol. This mixture is reacted with crystalline phosphoric acid or a phosphoric acid solution in amounts of from 75–100 mol %. The phosphoric acid may be dissolved or suspended in water, a $C_1$- to $C_5$-alcohol such as methanol, ethanol, propanol, isopropanol, or mixtures thereof. Preferably, ethanol, propanol, or isopropanol are used as the solvents.

The N-methyl-o-phenylenediamine-phosphoric acid salts are either precipitated from the solvent or may optionally be precipitated by the addition of non-polar solvents such as aliphatic or aromatic hydrocarbons or ethers.

In a preferred process, anhydrous phosphoric acid is used.

An alternative embodiment of the invention relates to processes in which N-methyl-o-phenylenediamine is prepared in situ by reduction of the o-nitro-N-methylaniline.

The reduction of the o-nitro-N-methylaniline may be carried out using methods known from the prior art. The preferred reducing agent is hydrogen, using a hydrogenation catalyst in an alcohol as solvent, preferably ethanol, propanol, or isopropanol. After the catalyst has been removed, the resulting solution can be reacted with phosphoric acid or a phosphoric acid solution. Preferably, a suspension of crystalline, anhydrous phosphoric acid in the alcohol used for hydrogenation is used.

EXAMPLE 1

A mixture of 190 kg of o-nitro-N-methylaniline, 0.95 kg of palladium/charcoal catalyst (10% Pd) and 570 L of ethanol is hydrogenated in a 1200 L-VA-Hydrogenator at 60 - max. of 85° C. under a hydrogen pressure of 2–6 bar until the uptake of hydrogen has stopped. 99 kg of crystalline phosphoric acid and 238 L of ethanol are placed in another 1200 L apparatus and the contents of hydrogenation apparatus are allowed to flow into it, with stirring, while the catalyst is filtered off.

The filter and the filtered catalyst are washed with 95 L of ethanol, cooled to 10–20° C., and stirred for a further 30–60 minutes. The product is centrifuged, washed with 238 L of ethanol and dried in vacuo at 40–60° C.

Yield: 230 kg of N-methylphenylenediamine, 0.77 phosphate (92% of theory).

The product typically contains 1.0–1.5% water. According to titration, a content of 61.0% N-methylphenylenediamine and 37.7% phosphoric acid is calculated.

Elemental analysis: C: 42.00% H: 6.34% N: 14.00% P: 11.92%

EXAMPLE 2

A mixture of 190 kg of o-nitro-N-methylaniline, 0.95 kg of palladium/charcoal catalyst (10% Pd) and 570 L of isopropanol is hydrogenated in a 1200 L-VA-Hydrogenator at 60 - max. of 85° C. under a hydrogen pressure of 2–6 bar until the uptake of hydrogen has stopped. 99 kg of crystalline phosphoric acid and 238 L of isopropanol are placed in another 1200 L apparatus and the contents of hydrogenation apparatus are allowed to flow into it, with stirring, while the catalyst is filtered off.

The filter and the filtered catalyst are washed with 95 L of isopropanol, cooled to 10–20° C., and stirred for a further 30–60 minutes. The product is centrifuged, washed with 238 L of isopropanol, and dried in vacuo at 40–60° C.

Yield: 225 kg of N-methylphenylenediamine, 0.77 phosphate (90% of theory)

According to titration a content of 61.1% N-methylphenylenediamine and 37.6% phosphoric acid is calculated.

Elemental analysis: C: 41.98% H: 6.35% N: 14.04% P: 11.93%

What is claimed is:
1. The phosphoric acid salt of N-methyl-o-phenylenediamine.
2. The phosphoric acid salt of N-methyl-o-phenylenediamine according to claim 1 having the general Formula I

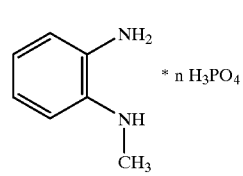

wherein n is a number between 0.5 and 1.0.
3. The phosphoric acid salt of N-methyl-o-phenylenediamine according to claim 2, wherein n is between 0.7 and 0.8.
4. The phosphoric acid salt of N-methyl-o-phenylenediamine according to claim 3, wherein n is between 0.75 and 0.78.
5. A process for preparing a phosphoric acid salt of N-methyl-o-phenylenediamine according to claim 1, the process comprising:
 (a) dissolving the N-methyl-o-phenylenediamine in a first solvent; and
 (b) reacting the dissolved N-methyl-o-phenylenediamine with crystalline phosphoric acid or phosphoric acid dissolved in a second solvent.
6. The process according to claim 5, wherein the N-methyl-o-phenylenediamine is prepared in situ.
7. The process according to claim 6, wherein the o-N-methylphenylenediamine is prepared in situ from o-nitro-N-methylaniline.
8. The process according to claim 5, wherein the first solvent is a $C_1$- to $C_5$-alcohol.
9. The process according to claim 5, wherein the first solvent and the second solvent are the same.
10. The process according to claim 9, wherein the first solvent and the second solvent are selected from the group consisting of ethanol, propanol, or isopropanol.
11. A process for preparing a phosphoric acid salt of N-methyl-o-phenylenediamine according to claim 2, the process comprising:
 (a) dissolving the N-methyl-o-phenylenediamine in a first solvent; and
 (b) reacting the dissolved N-methyl-o-phenylenediamine with crystalline phosphoric acid or phosphoric acid dissolved in a second solvent.
12. The process according to claim 11, wherein the N-methyl-o-phenylenediamine is prepared in situ.
13. The process according to claim 12, wherein the o-N-methylphenylenediamine is prepared in situ from o-nitro-N-methylaniline.
14. The process according to claim 11, wherein the first solvent is a $C_1$- to $C_5$-alcohol.
15. The process according to claim 11, wherein the first solvent and the second solvent are the same.
16. The process according to claim 15, wherein the first solvent and the second solvent are selected from the group consisting of ethanol, propanol, or isopropanol.
17. A process for preparing a phosphoric acid salt of N-methyl-o-phenylenediamine according to claim 3, the process comprising:
 (a) dissolving the N-methyl-o-phenylenediamine in a first solvent; and (b) reacting the dissolved N-methyl-o-phenylenediamine with crystalline phosphoric acid or phosphoric acid dissolved in a second solvent.

18. The process according to claim 17, wherein the N-methyl-o-phenylenediamine is prepared in situ.

19. The process according to claim 18, wherein the o-N-methylphenylenediamine is prepared in situ from o-nitro-N-methylaniline.

20. The process according to claim 17, wherein the first solvent is a $C_1$- to $C_5$-alcohol.

21. The process according to claim 17, wherein the first solvent and the second solvent are the same.

22. The process according to claim 21, wherein the first solvent and the second solvent are selected from the group consisting of ethanol, propanol, or isopropanol.

* * * * *